(12) United States Patent
Zimmer

(10) Patent No.: US 7,799,578 B2
(45) Date of Patent: *Sep. 21, 2010

(54) CAPILLARY ACTIVE TEST ELEMENT HAVING AN INTERMEDIATE LAYER SITUATED BETWEEN THE SUPPORT AND THE COVERING

(75) Inventor: Volker Zimmer, Dossenheim (DE)

(73) Assignee: Roche Diagnostics GmbH, Mannheim (DE)

( * ) Notice: Subject to any disclaimer, the term of this patent is extended or adjusted under 35 U.S.C. 154(b) by 60 days.

This patent is subject to a terminal disclaimer.

(21) Appl. No.: 11/807,548

(22) Filed: May 29, 2007

(65) Prior Publication Data

US 2007/0266803 A1 Nov. 22, 2007

Related U.S. Application Data

(63) Continuation of application No. 09/554,793, filed as application No. PCT/EP98/07854 on Dec. 3, 1998, now Pat. No. 7,238,534.

(30) Foreign Application Priority Data

Dec. 4, 1997  (DE) ................................ 197 53 850

(51) Int. Cl.
*G01N 1/10* (2006.01)
*B01L 3/02* (2006.01)

(52) U.S. Cl. .................. 436/174; 436/165; 422/61; 422/100

(58) Field of Classification Search ................ 422/100, 422/61; 436/165, 174
See application file for complete search history.

(56) References Cited

U.S. PATENT DOCUMENTS

| 3,715,192 A | 2/1973 | Wenz et al. |
| 4,138,216 A | 2/1979 | Larsson et al. |
| 4,250,257 A | 2/1981 | Lee et al. |
| 4,254,083 A | 3/1981 | Columbus |
| 4,312,834 A | 1/1982 | Vogel et al. |
| 4,323,536 A | 4/1982 | Columbus |
| 4,353,923 A | 10/1982 | Takizawa et al. |
| 4,354,308 A | 10/1982 | Shimada et al. |
| 4,439,526 A | 3/1984 | Columbus |
| 4,588,624 A | 5/1986 | Nygren et al. |
| 4,654,197 A | 3/1987 | Lilja et al. |
| 4,826,772 A | 5/1989 | Meathrel |

(Continued)

FOREIGN PATENT DOCUMENTS

DE     19753850     *  6/1999

(Continued)

*Primary Examiner*—Lyle A Alexander
(74) *Attorney, Agent, or Firm*—Woodard, Emhardt, Moriarty McNett & Henry LLP

(57) ABSTRACT

The invention concerns a device and method for withdrawing samples of liquid samples for analytical elements. The device includes a carrier and a cover with a surface that cooperates with a surface of the carrier to form a channel. The channel has an opening defined by at least one edge. At least one notch in the form of a partial groove extends into the at least one edge of the opening so that one side of the edge of the opening is at least partially interrupted by the at least one notch. The notch forms a sample application opening by exposing the surface, whose extension forms an inner surface of the channel.

20 Claims, 4 Drawing Sheets

U.S. PATENT DOCUMENTS

| | | | |
|---|---|---|---|
| 4,870,000 A | 9/1989 | Bergthaller et al. | |
| 4,900,663 A | 2/1990 | Wie et al. | |
| 4,933,092 A | 6/1990 | Anet et al. | |
| 4,943,415 A | 7/1990 | Przybylowicz et al. | |
| 4,952,373 A | 8/1990 | Sugarman et al. | |
| 5,006,474 A | 4/1991 | Horstman et al. | |
| 5,071,746 A | 12/1991 | Wilk et al. | |
| 5,100,627 A | 3/1992 | Buican et al. | |
| 5,126,247 A | 6/1992 | Palmer et al. | |
| 5,147,606 A | 9/1992 | Charlton et al. | |
| 5,173,433 A | 12/1992 | Bachand | |
| 5,192,502 A | 3/1993 | Attridge et al. | |
| 5,208,163 A | 5/1993 | Charlon et al. | |
| 5,264,103 A | 11/1993 | Yoshioka et al. | |
| 5,271,895 A | 12/1993 | McCroskey et al. | |
| 5,308,775 A | 5/1994 | Donovan et al. | |
| 5,310,525 A | 5/1994 | Churchouse et al. | |
| 5,395,504 A | 3/1995 | Saurer et al. | |
| 5,395,506 A | 3/1995 | Duce et al. | |
| 5,399,316 A | 3/1995 | Yamada | |
| 5,405,511 A | 4/1995 | White et al. | |
| 5,437,999 A | 8/1995 | Diebold et al. | |
| 5,575,895 A | 11/1996 | Ikeda et al. | |
| 5,611,995 A | 3/1997 | de Zoeten et al. | |
| 5,714,123 A | 2/1998 | Sohrab | |
| 5,741,634 A | 4/1998 | Nozoe et al. | |
| 5,759,364 A | 6/1998 | Charlton et al. | |
| 5,762,770 A | 6/1998 | Pritchard et al. | |
| 5,814,522 A | 9/1998 | Zimmer et al. | |
| 5,843,691 A | 12/1998 | Douglas et al. | |
| 5,846,837 A | 12/1998 | Thym et al. | |
| 5,851,838 A | 12/1998 | Vetter et al. | |
| 5,942,102 A | 8/1999 | Hodges et al. | |
| 5,962,215 A | 10/1999 | Douglas et al. | |
| 5,997,817 A | 12/1999 | Crismore et al. | |
| 6,025,203 A | 2/2000 | Vetter et al. | |
| 6,036,919 A | 3/2000 | Thym et al. | |
| 6,104,484 A | 8/2000 | Nagata et al. | |
| 6,165,416 A | 12/2000 | Chandler | |
| 6,174,420 B1 | 1/2001 | Hodges et al. | |
| 6,179,979 B1 | 1/2001 | Hodges et al. | |
| 6,194,220 B1 | 2/2001 | Malick et al. | |
| 6,207,000 B1 * | 3/2001 | Schwobel et al. | 156/248 |
| 6,238,624 B1 | 5/2001 | Heller et al. | |
| 6,325,975 B1 | 12/2001 | Naka et al. | |
| 6,592,815 B1 | 7/2003 | Zimmer | |
| 6,696,024 B1 | 2/2004 | Leichner et al. | |
| 7,008,799 B1 | 3/2006 | Zimmer | |

FOREIGN PATENT DOCUMENTS

| | | |
|---|---|---|
| EP | 0 010 456 A1 | 4/1980 |
| EP | 0 852 336 A1 | 7/1998 |
| GB | 2090659 A | 7/1982 |
| WO | WO 9822625 | 5/1998 |

* cited by examiner

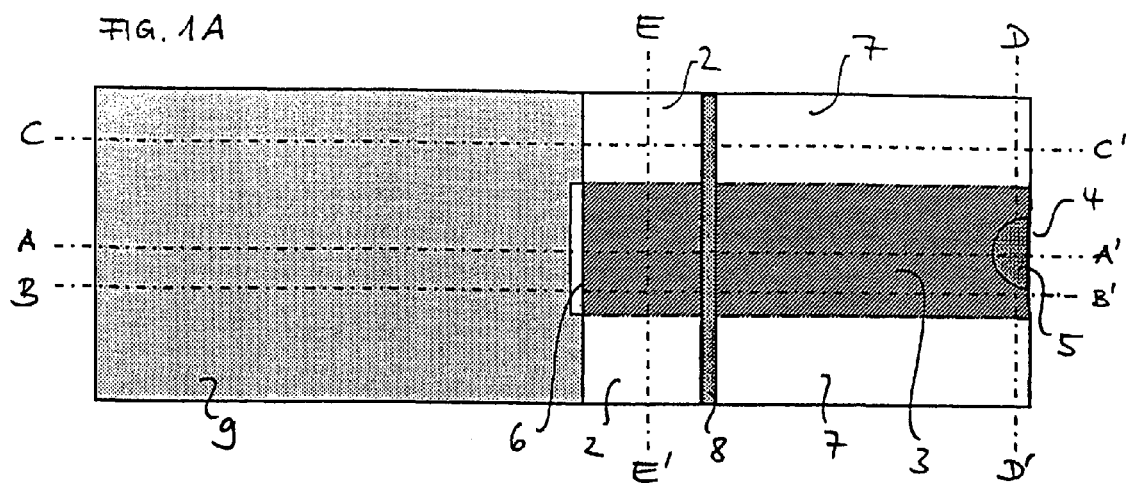
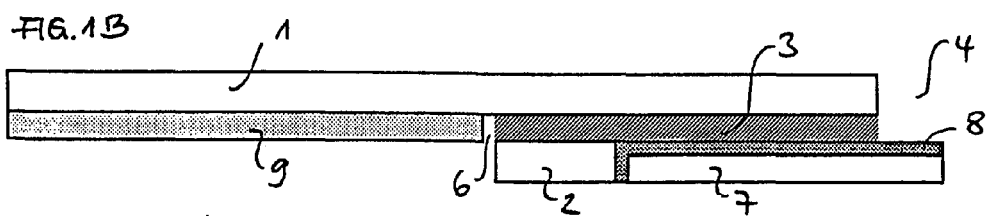
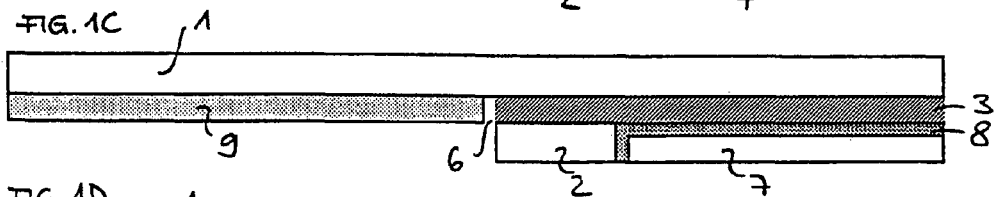
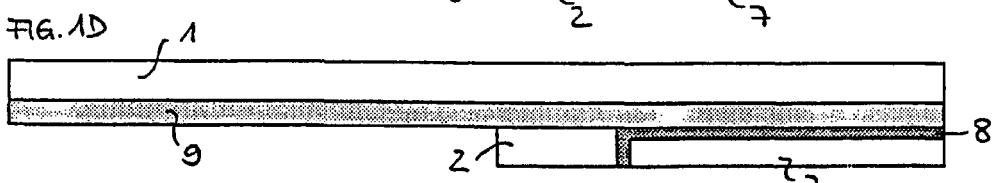
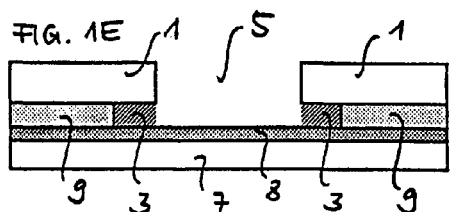
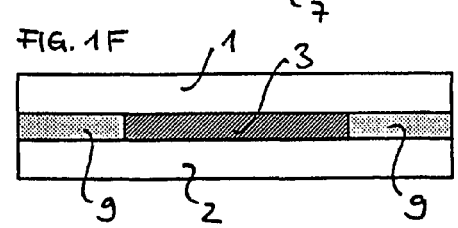
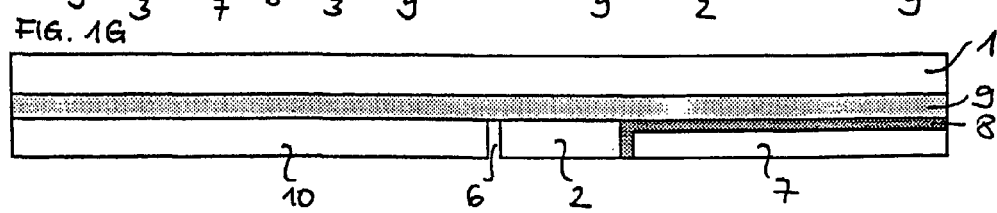

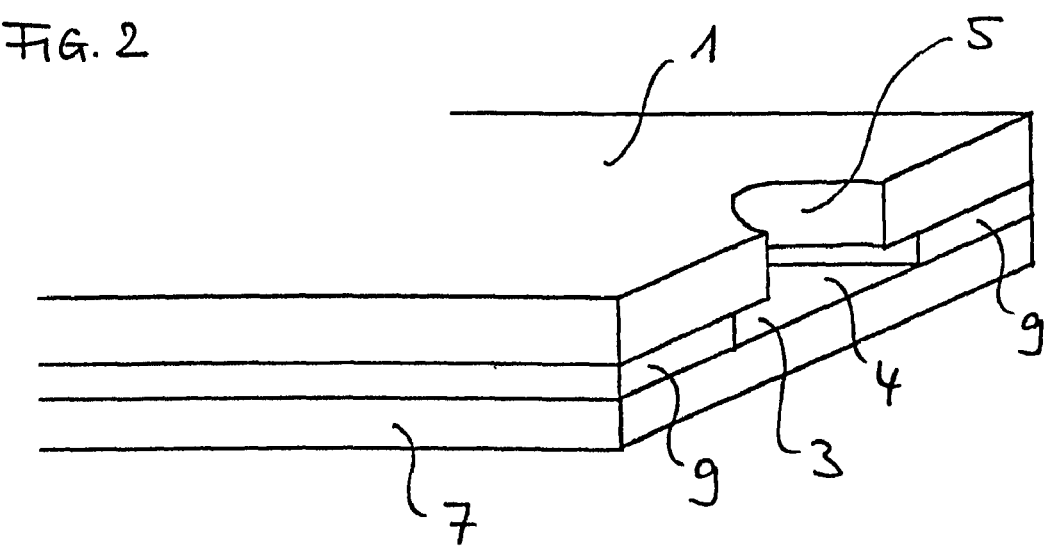

CAPILLARY ACTIVE TEST ELEMENT HAVING AN INTERMEDIATE LAYER SITUATED BETWEEN THE SUPPORT AND THE COVERING

REFERENCE TO RELATED APPLICATIONS

The present application is a continuation of U.S. application Ser. No. 09/554,793 filed Sept. 19, 2000, now U.S. Pat. No. 7,238,534 and which claims priority to PCT Application No. PCT/EP98/07854 filed Dec. 3, 1998 and German Patent Application No. 19753850.9, filed Dec. 4, 1997, each of which is hereby incorporated by reference in its entirety.

TECHNICAL FIELD

The present invention is within the field of sample liquid analysis by test elements.

BACKGROUND

The invention concerns a device for withdrawing samples of liquid samples for analytical elements in which the sample is transported in the analytical element in a capillary-active channel from a sample application opening to the determination site for the sample and in which the capillary-active channel is essentially formed by a carrier, a cover and optionally an intermediate layer lying between the cover and carrier. In addition the invention concerns a process for withdrawing a liquid sample into an analytical element with the aid of the said device.

So-called carrier-bound tests are often used for the qualitative or quantitative analytical determination of components of body fluids, in particular of blood. In these the reagents are embedded in corresponding layers of a solid carrier which is contacted with the sample. If a target analyte is present, the reaction of the liquid sample and reagents leads to a detectable signal, in particular a colour change which can be evaluated visually or with the aid of an instrument, usually by reflection photometry.

Test elements or test carriers are often in the form of test strips which are essentially composed of an elongated carrier layer made of plastic material and detection layers which are applied thereto as test fields. However, test carriers are also known which are in the shape of small quadratic or rectangular plates.

Test elements for clinical diagnostics that are evaluated visually or by reflection photometry are frequently constructed like electrochemical sensors and biosensors such that the sample application zone and the detection zone are arranged one above the other in a vertical axis. This mode of construction is problematic. When the test strip loaded with sample has to be inserted into an instrument, for example a reflection photometer, for measurement, potentially infectious sample material can come into contact with parts of the instrument and may contaminate them. Furthermore volumetric dosing can only be achieved with difficulty especially in cases in which the test strips are used by untrained persons for example in the self-control of blood sugar by diabetics.

Recently test elements have become available which provide a capillary channel or gap with the aid of which at least some of the described problems can be solved.

EP-B-0 034 049 concerns a test element in which the sample is applied to a central sample application site for example an opening in a cover and is transported by capillary force to several detection zones which are spatially separated from the sample application site. In this case it is remarkable that a special design for the geometry of the sample application opening which is also described in EP-B-0 010 456 is emphasized as being particularly preferable. A regular hexagonal shape of the sample entry opening in top view is claimed to centre a drop of liquid sample in the opening. This is claimed to facilitate penetration of the sample into the capillary-active channel which is perpendicular to the sample application opening.

Whereas in the described capillary gap test elements the sample is applied through an opening in the test element which is perpendicular to the capillary gap, in other designs the sample liquid is applied directly into the capillary gap parallel to the direction of spread. This is most simply accomplished by the test element having an edge where the capillary gap ends and which is directly contacted with a sample liquid. When contacted with the edge, the sample liquid is taken up by the channel which is capable of capillary liquid transport.

A frequent problem with the latter test elements is that liquid drops which are applied to the sample application opening of the capillary gap are not able to penetrate into the gap. This phenomenon can have different causes. It is conceivable that in the manufacture of such test elements the opening for fabrication reasons does not have the dimensions that are required for a sample drop to enter into the capillary channel for example because the opening has been contaminated or squashed when the test element was cut to length or stamped out. Another reason may be that the hydrophobicity of the materials which are often used to manufacture the said test elements such as for example hydrophobic plastics, impair, delay or prevent penetration of the sample into the capillary gap. For example a liquid drop already does not enter into the inside of a capillary channel or only very slowly if its inner surfaces are indeed hydrophilic but the cut edge is hydrophobic due to the materials used.

The object of the present invention was to eliminate the disadvantages of the prior art.

This is achieved by the subject matter of the invention as characterized in the patent claims.

SUMMARY

The invention concerns a device and method for withdrawing samples of liquid samples for analytical elements. The device includes a carrier and a cover with a surface that cooperates with a surface of the carrier to form a channel. The channel has an opening defined by at least one edge. At least one notch in the form of a partial groove extends into the at least one edge of the opening so that one side of the edge of the opening is at least partially interrupted by the at least one notch. The notch forms a sample application opening by exposing the surface, whose extension forms an inner surface of the channel.

The device according to the invention contains one such notch. However, other designs can also be realized in which several and at least two notches are present together in one surface or are offset on opposite surfaces. There are no limits to the shape of the notches provided at least part of the edge which forms the sample application opening is at least partially interrupted by the notch. Hence triangular or polygonal as well as round or elliptical forms are possible. Irregular shapes are also not excluded.

The notch in a surface forming the capillary channel at the edge of the test element which forms the sample application opening serves to ensure that the sample liquid can enter into the capillary channel. This is achieved in that the sample drop can be directly applied to one of the surfaces, whose extension forms the inner surface of the capillary, at the edge of the device that is broken by the notch which is nearest the sample application opening. Suitable selection of the geometry and dimensions of the notch ensures that the liquid drop comes into contact with the capillary active zone with very high probability, independent of the exact position of the dosing and is readily sucked into the inside of the capillary. For example the size of the exposed surface should be selected such that at least one site of the liquid drop that is applied thereto comes into contact with the capillary-active zone. For example one dimension of the notch, such as its width, should be selected such that the diameter of the liquid drop is slightly larger than the selected dimension of the notch. A notch width of 1 mm has proven to be suitable for a drop of 3 µl. Suction of the sample drop into the capillary channel is achieved by the area exposed by the notch being hydrophilized and bordering directly on a capillary active zone at least in the direction of the capillary transport channel.

In this connection hydrophilic surfaces are water-attracting surfaces. Aqueous samples, also including blood, spread well on such surfaces. Such surfaces are characterized among others in that a water drop placed on it forms an acute rim angle or contact angle at the interface. In contrast an obtuse rim angle is formed at the interface between the water drop and the surface on hydrophobic surfaces.

The rim angle which is a result of the surface tensions of the test liquid and of the surface to be examined is a measure of the hydrophilicity of a surface. Water for example has a surface tension of 72 mN/m. If the value of the surface tension of the observed surface is much below this value i.e. more than 20 mN/m, then the wetting is poor and the resulting rim angle is obtuse. Such a surface is referred to as hydrophobic. If the surface tension approximates the value which is found for water then the wetting is good and the rim angle is acute. If, in contrast, the surface tension is the same as or higher than that of the value found for water, then the drop runs and there is a total spreading of the liquid. It is then no longer possible to measure a rim angle. Surfaces which form an acute rim angle with water drops or on which a total spreading of a water drop is observed are referred to as hydrophilic.

The ability of a capillary to suck up a liquid depends on the wettability of the channel surface with the liquid. This means for aqueous samples that a capillary should be manufactured from a material whose surface tension almost reaches 72 mN/m or exceeds this value.

Sufficiently hydrophilic materials for the construction of a capillary which rapidly sucks up aqueous samples are for example glass, metal or ceramics. However, these materials are unsuitable for use in test carriers since they have some severe disadvantages such as risk of breaking in the case of glass or ceramics or change in the surface properties with time in the case of numerous metals. Therefore plastic foils or moulded parts are usually used to manufacture test elements. As a rule the plastics used hardly exceed a surface tension of 45 mN/m Even with the, in a relative sense, most hydrophilic plastics such as polymethylmethacrylate (PMMA) or polyamide (PA) it is only possible—if at all—to construct slowly sucking capillaries. Capillaries made of hydrophobic plastics such as for example polystyrene (PS), polypropylene (PP) or polyethylene (PE) essentially do not suck aqueous samples. Consequently it is necessary to endow the plastics used as a construction material for test elements with capillary active channels with hydrophilic properties i.e. to hydrophilize them In an embodiment of the analytical test element according to the invention at least one, but preferably two and especially preferably two opposite surfaces which form the inner surface of the channel capable of capillary liquid transport are hydrophilized. At least the exposed surface opposite the notch is very preferably hydrophilized. If more than one surface is hydrophilized then the surfaces can either be made hydrophilic using the same or different methods. Hydrophilization is particularly necessary when the materials that form the capillary active channel, in particular the carrier, are themselves hydrophobic or only very slightly hydrophilic because they are for example composed of nonpolar plastics. Nonpolar plastics such as for example polystyrene (PS), polyethylene (PE), polyethylene terephthalate (PET) or polyvinyl chloride (PVC) are advantageous as carrier materials because they do not absorb the liquids to be examined and thus the sample volume can be effectively utilized by the detection layer. The hydrophilization of the surface of the capillary channel enables a polar, preferably aqueous, sample liquid to readily enter the capillary channel and be rapidly transported to the site of determination of the sample. In this connection the site of determination is understood as that site or that zone to which the sample should be transported in the analytical element in order to achieve the desired result. If the analytical element is for example a test carrier that is to be evaluated optically or photometrically, the site of determination of the sample is the detection zone of the test carrier in which a reaction with a change in colour is observable. If the analytical element is an electrochemical sensor the site of determination of the sample is understood as an electrode integrated into the sensor which is capable of the desired electrochemical detection reaction. If the analytical element does not itself serve to detect an analyte in a sample, but for example is only used for volume dosing or taking up a certain amount of sample material, the site of determination of the sample can be simply a mark on the analytical element up to which the capillary gap has to be filled in order to for example measure a certain minimum sample volume.

Ideally the hydrophilizaton of the surface of the capillary channel is achieved by using a hydrophilic material in its manufacture which, however, cannot itself suck up the sample liquid or only to a negligible extent. In cases where this is not possible a hydrophobic or only very slightly hydrophilic surface can be hydrophilized by suitable coating with a stable hydrophilic layer that is inert towards the sample material for example by covalently binding photoreactive hydrophilic polymers onto a plastic surface by applying layers containing wetting agents or by coating surfaces with nanocomposites by means of sol-gel technology. Furthermore it is also possible to achieve an increased hydrophilicity by thermal, physical or chemical treatment of the surface.

The hydrophilization is quite especially achieved by using thin layers of oxidized aluminium. These layers are either applied directly to the desired components of the test element for example by vacuum coating the work pieces with metallic aluminium and subsequently oxidizing the metal, or by using metal foils or metal-coated plastics for the construction of the test carriers which also have to be oxidized to achieve the desired hydrophilicity. In this case metal layer thicknesses of 1 to 500 nm are adequate. The metal layer is subsequently oxidized in which case above all oxidation in the presence of water vapour or by boiling in water have proven to be especially suitable methods in addition to electrochemical, anodic oxidation. The oxide layers formed in this manner are between 0.1 and 500 nm, preferably between 10 and 100 nm thick depending on the method. Larger layer thicknesses of the metal layer as well as of the oxide layer can in principle be realized in practice but do not exhibit any additional advantageous effects.

A second subject matter of the invention concerns a process for withdrawing a liquid sample, in particular a body fluid such as blood, plasma, serum, urine, saliva, sweat etc.

with the aid of a device according to the invention. In this process the liquid sample is contacted with the device at the edge of the sample application opening which is interrupted by the notch. The sample liquid is transported into the inside of the device by capillary forces in the channel that is capable of capillary liquid transport so that it can reach its site of determination.

BRIEF DESCRIPTION OF THE DRAWINGS

The invention is elucidated in more detail by FIGS. 1-6 and by the following examples.

FIG. 1 shows a particularly preferred embodiment of the device according to the invention. A schematic top view of the device according to the invention is shown in FIG. 1A. FIGS. 1B to 1G each show cross-sectional views along the lines A-A'(1B), B-B'(1C), C-C'(1D and 1G), D-D'(1E) and E-E' (1F) respectively.

FIG. 2 shows a perspective detailed enlargement of the sample application region of the device according to the invention.

DETAILED DESCRIPTION OF THE DRAWINGS

Figure 3:
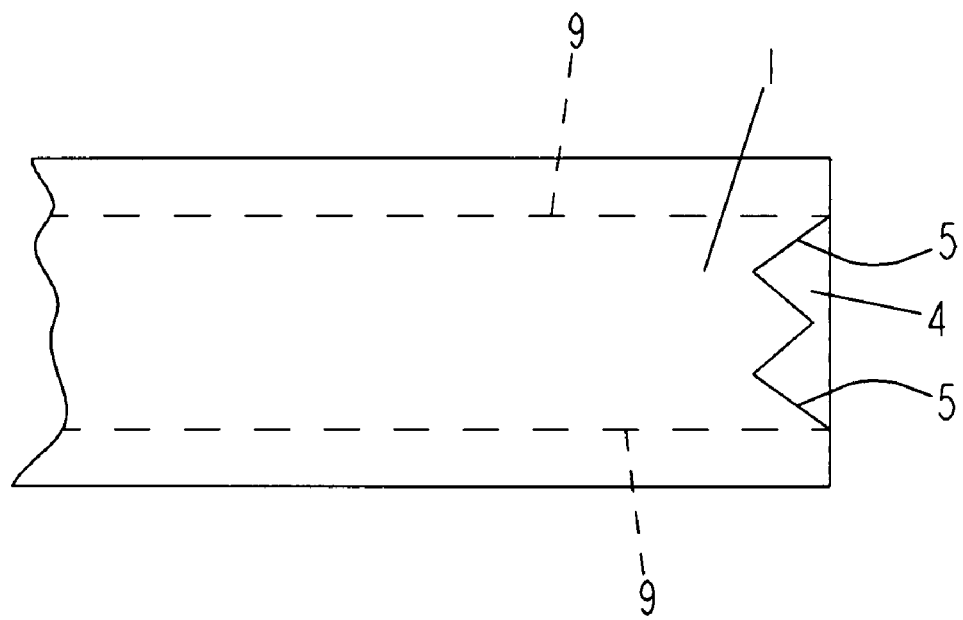
FIG. 3 shows a plan view of a device in accordance with the present invention.
Figure 4:
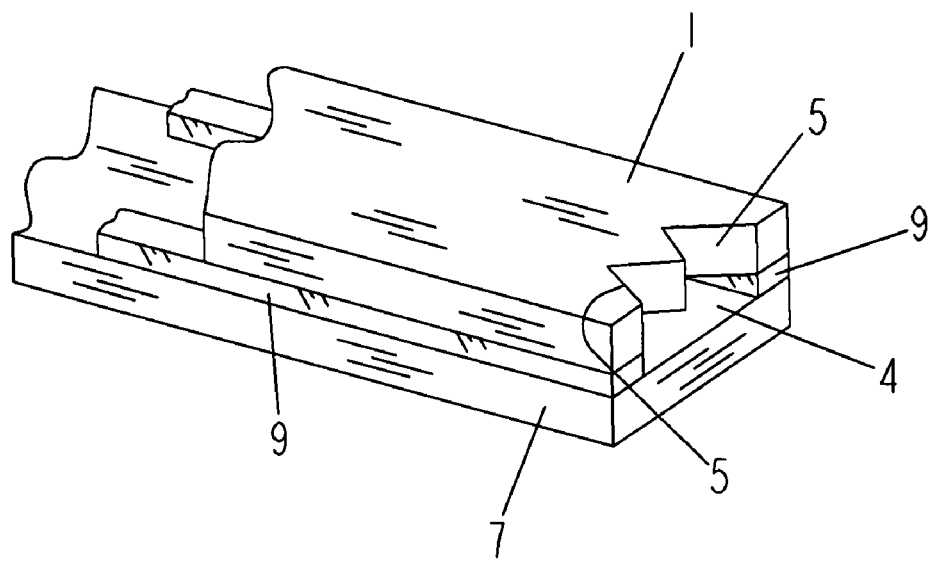
FIG. 4 shows an enlarged perspective view of the device of FIG. 3.
Figure 5:
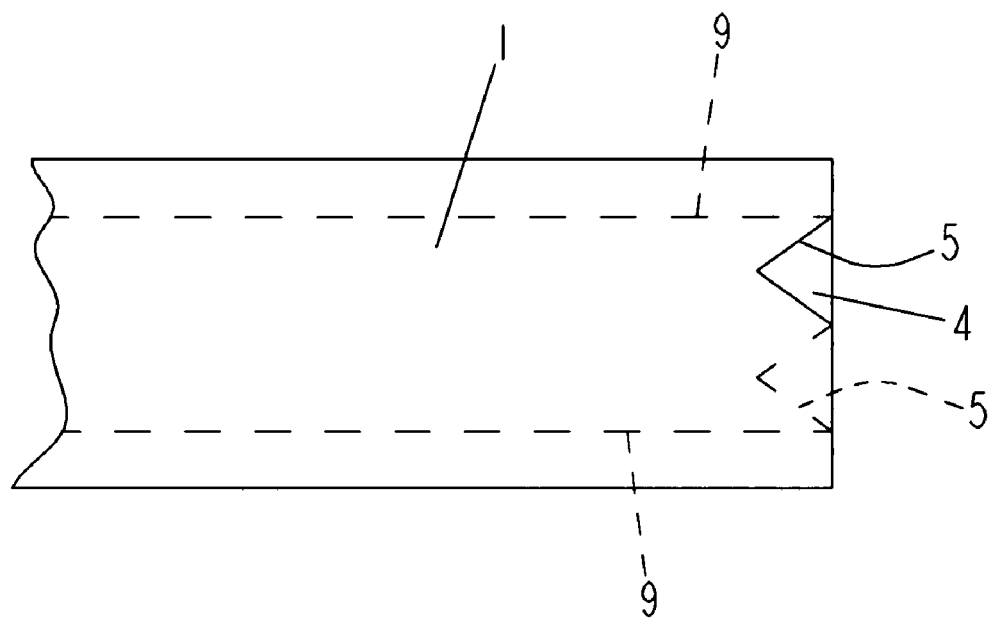
FIG. 5 shows a plan view of a device in accordance with the present invention.
Figure 6:
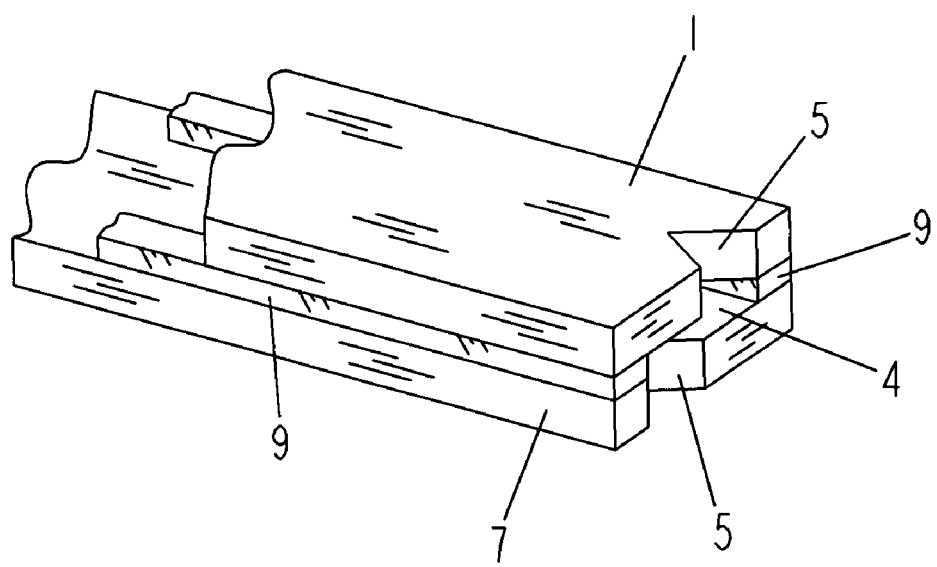
FIG. 6 shows an enlarged perspective view of device of FIG. 5.

The numbers in the Figures denote:
1 carrier
2 detection element
3 capillary channel
4 sample application opening
5 notch for sample application
6 vent opening
7 cover
8 gap cover foil
9 intermediate layer
10 support foil Various views (FIGS. 1A to 1F) of a particularly preferred embodiment of the device according to the invention are shown schematically in FIG. 1. The views shown are intended to give a three-dimensional impression of the device according to the invention. An intermediate layer (9) is mounted on a carrier (1) for example in the form of a double-sided adhesive tape. In the area of the capillary channel (3) the intermediate layer (9) has a recess which determines the length and width of the channel (3). Its height is given by the thickness of the intermediate layer (9). On the side of the capillary channel (3) which is opposite to the carrier (1), a cover (7) e.g. a plastic foil is located adjacent to the detection element (2) e.g. a reagent-impregnated membrane. A gap cover foil (8) is provided to ensure capillary continuity between the detection element and cover. This can be hydrophilized to enable a rapid transport of sample from the sample application opening (4) to the vent opening (6) which marks the opposite end of the capillary channel. An additional advantage of the hydrophilization is that a drop of sample liquid can be applied directly to a hydrophilic surface in the area of the notch (5) which is surrounded on several boundary sides by the capillary active zone (3). This leads to a rapid penetration of the liquid drop into the test element.

The capillary zone (3) extends from the sample application opening (4) to the opposite end of the detection element (2) and thus ensures that the sample liquid can contact the whole area of the detection element (2). The capillary zone (3) further ensures that a homogeneous sample distribution over the detection element (2). The sample application opening (4) and vent opening (6) limit the capillary active region (3) in the direction of capillary transport.

FIG. 1G shows how the intermediate layer (9) can be covered by a supporting foil (10) in order to cover areas of the adhesive tape that are exposed. However, the vent opening (6) must not be covered.

When using the device shown, its sample application opening (4) is for example contacted with a blood drop located on a fingertip. In this connection it is unimportant whether the blood drop comes into contact with the device according to the invention containing the sample application opening (4) from above i.e. on the flat side of the carrier (1) or from the front i.e. from the front side of the test element. This largely rules out an erroneous application of sample which would for example be expected of users that are used to conventional test strips that have to be dosed from above. When the device according to the invention is used the blood drop comes into contact with the exposed surface which is optionally hydrophilized and simultaneously with the capillary channel (3) through the notch (5) in the carrier (1). The capillary channel fills itself with sample until it is filled from the sample application opening (4) to the vent opening (6). Afterwards the device is removed from the patient's finger which ensures that only the sample that is present in the capillary channel (3) is available for the detection element (2). Thus overdosing is excluded. The defined height of the capillary channel provides a defined layer thickness of the sample on the detection element.

A detailed enlargement of a perspective view of the sample application area of a particularly preferred embodiment of the test element according to the invention is shown in FIG. 2. The notch (5) in the carrier (1) facilitates penetration of a sample liquid from the sample application opening (4) into the capillary active zone (3) which in the present case is formed by the carrier (1), intermediate layer (9) and cover (7). In addition to the shape shown the notch can also have any other desired shape which serves the purpose according to the invention. Among others semicircular, triangular or polygonal shapes and the use of one or several adjacent staggered opposing notches are possible.

EXAMPLE 1

Manufacture of the Analytical Test Element According to the Invention

A double-sided adhesive tape with a thickness of 100 µm is glued onto a 350 µm thick foil of polyethylene terephthalate (MELINEX®, ICI, Frankfurt am Main, Germany) coated with a 30 nm thick layer of aluminium which was completely oxidized with water vapour. The foil has a length of 25 mm and is 5 mm wide. A central notch-shaped recess of 1 mm width and 2 mm length is located on one of the short sides. The adhesive tape has a punched hole of 2 mm width and more than 15 mm length which defines the dimensions of the capillary channel. The length of the punched hole is selected to be slightly larger than the desired length of the capillary-active channel which is determined by its cover in order to ensure venting of the channel during filling with sample liquid. A 3 mm long and 5 mm wide detection film is glued onto the side of the adhesive tape which provides the venting at a distance of 1 mm from the end of the punched hole. A film is used as the detection film as is known from the German Patent Application No. P 196 29 656.0, also published as U.S. Pat. No. 6,036,919. The detection film is specific for the detection of glucose. A 12 mm long and 5 mm wide cover layer is glued onto the region of the adhesive tape that is still open between the notch-shaped recess and detection film so that the cover layer and detection film abut one another. The cover layer is composed of a 150 µm thick polyethylene terephthalate foil provided on one side with adhesive onto which a 6 µm thick polyethylene terephthalate foil (both: HOSTAPHAN®, Hoechst, Frankfurt am Main, Germany) coated with a 30 nm thick oxidized aluminium layer on the side facing the capillary channel is glued. In this case the thinner foil extends ca. 500 µm beyond the thicker foil on the side facing the detection film When the cover layer is mounted on the adhesive tape care must be taken that the protruding end of the thinner foil comes to lie between the detection element and the thicker foil of the cover layer. In order to cover areas of the adhesive foil that are still exposed, these are covered with a 175 µm thick MELINEX® foil without, however, covering functional areas.

The test element obtained in this manner has a capillary channel of 15 mm length, 2 mm width and 0.1 mm height. The channel can take up 3 µl sample liquid. An area of 3 mm×2 mm of the detection film is wetted by the sample.

EXAMPLE 2

Measurement of the blood glucose concentration with the aid of the test element from example 1

The sample application side of the test element from example 1 is placed on a drop of sample liquid. The capillary of the test element automatically fills with sample within 2 s. If glucose is present in the sample a colour development is visible in the detection film after a few seconds. The end point of the reaction is reached after ca. 30 to 35 s. The colour obtained can be correlated with the glucose concentration of the sample and either evaluated visually or by reflection photometry.

What is claimed is:

1. A device for withdrawing samples of liquid samples for analytical elements, wherein the device comprises:
    a carrier and
    a cover having a surface that cooperates with a surface of the carrier to form a channel, the channel having an opening located generally at one end of the device and generally defined by opposing edges of the carrier and the cover,
    wherein at least one notch in the form of a partial groove extends into at least one of the edges of the opening of the channel so that one side of the edge of the opening is at least partially interrupted by the at least one notch, and the notch forming the sample opening so that a surface opposite to the notch is exposed, the exposed surface forming an inner surface of the channel.

2. Device as claimed in claim 1, wherein at least two notches are located next to one another.

3. Device as claimed in claim 1, wherein notches are staggered on opposite sides.

4. Device as claimed in claim 1, wherein at least one of the surfaces forms an inner surface of the channel that is capable of capillary liquid transport and is hydrophilized.

5. Device as claimed in claim 4, wherein an exposed surface opposite to the notch is hydrophilized.

6. Device as claimed in claim 5, wherein a layer of oxidized aluminum is used for the hydrophilization.

7. Device as claimed in claim 4, further comprising a second cover and an intermediate layer positioned between the second cover and the carrier.

8. Device as claimed in claim 4, wherein the hydrophilization is achieved by a hydrophilic material.

9. Device as claimed in claim 4, wherein the hydrophilization is achieved by a hydrophilic layer.

10. Device as claimed in claim 6, wherein the hydrophilization is achieved by a hydrophilic layer.

11. Device as claimed in claim 10, wherein a layer of oxidized aluminum is used for the hydrophilization.

12. A method for withdrawing a liquid sample into an analytical element, the method comprising the steps of
    proving a device that comprises a carrier and a cover having a surface that cooperates with a surface of the carrier to form a capillary-active channel having a sample application opening located generally at one end of the device and defined by opposing edges of the carrier and the cover and wherein at least one notch in the form of a partial groove extends into at least one of the edges of the sample application opening of the channel so that one side of the edge of the sample application opening is at least partially interrupted by the at least one notch and the notch forming the sample opening so that a surface opposite to the notch is exposed, the exposed surface comprises a capillary active zone at least in the direction of the capillary-active channel, and
    contacting the edge of the sample application opening adjacent to the notch with the liquid sample so that at least one site of a liquid drop comes into contact with the capillary active zone and the liquid sample is transported by capillary forces into the channel.

13. Device as claimed in claim 12, wherein at least two notches are located next to one another.

14. Device as claimed in claim 12, wherein at least two notches are staggered on opposite sides.

15. Device as claimed in claimed 12, wherein at least one of the surfaces forms an inner surface of the channel capable of capillary liquid transport and is hydrophilized.

16. A device for withdrawing samples of liquid samples for analytical elements, wherein the device comprises:
    a carrier and
    a cover having a surface that cooperates with a surface of the carrier to form a capillary-active channel,
    wherein at least one notch in one of the carrier and the cover forms a sample application opening to the channel by exposing a portion of the surface of the other of the carrier and the cover, said notch forming the sample opening so that a surface opposite to the notch is exposed, wherein the exposed portion forms an inner surface of the channel, the notch bordering directly on a capillary active zone at least in the direction of the capillary-active channel.

17. Device as claimed in claim 16, wherein at least two notches are located next to one another.

18. Device as claimed in claim 17, wherein notches are staggered on opposite sides.

19. Device as claimed in claim 16, wherein at least one of the surfaces forms an inner surface of the channel capable of capillary liquid transport and is hydrophilized.

20. Device as claimed in claim 19, wherein a layer of oxidized aluminum is used for the hydrophilization.

* * * * *